United States Patent
Harrington et al.

(10) Patent No.: US 10,271,787 B2
(45) Date of Patent: Apr. 30, 2019

(54) MULTICAPACITOR SENSOR ARRAY WITH USER ELECTRICAL FEEDBACK

(71) Applicant: RTC Inc., Dexter, MI (US)

(72) Inventors: Richard H. Harrington, Dexter, MI (US); Michael Rontal, Bloomfield Hills, MI (US); Charles W. Krapf, Livonia, MI (US); Frank J. Fedel, Royal Oak, MI (US); Doug Briggs, Waukesha, WI (US)

( * ) Notice: Subject to any disclaimer, the term of this patent is extended or adjusted under 35 U.S.C. 154(b) by 0 days.

(21) Appl. No.: 15/254,628

(22) Filed: Sep. 1, 2016

(65) Prior Publication Data

US 2017/0055902 A1 Mar. 2, 2017

Related U.S. Application Data

(60) Provisional application No. 62/212,896, filed on Sep. 1, 2015.

(51) Int. Cl.
| | |
|---|---|
| *A61B 5/04* | (2006.01) |
| *A61B 5/00* | (2006.01) |
| *A61N 1/04* | (2006.01) |
| *A61N 1/36* | (2006.01) |

(52) U.S. Cl.
CPC ............ *A61B 5/4851* (2013.01); *A61B 5/486* (2013.01); *A61N 1/0456* (2013.01); *A61N 1/0476* (2013.01); *A61N 1/36003* (2013.01)

(58) Field of Classification Search
None
See application file for complete search history.

(56) References Cited

U.S. PATENT DOCUMENTS

| | | | | |
|---|---|---|---|---|
| 2002/0198604 A1* | 12/2002 | Schulman | ............ | A61B 5/0031 623/25 |
| 2010/0016990 A1* | 1/2010 | Kurtz | ........................ | A61F 2/58 623/24 |
| 2012/0101595 A1* | 4/2012 | Jung | ........................ | A61F 2/68 623/25 |
| 2012/0109013 A1* | 5/2012 | Everett | ................ | A61B 5/1036 600/587 |
| 2014/0031952 A1* | 1/2014 | Harshbarger | ............. | A61F 2/54 623/25 |
| 2014/0088664 A1* | 3/2014 | Sharma | .............. | A61N 1/36007 607/48 |

(Continued)

*Primary Examiner* — Ankit D Tejani
(74) *Attorney, Agent, or Firm* — John G. Posa; Belzer P.C.

(57) ABSTRACT

Electrical feedback is provided to a user who cannot receive full sensation from a body part due to amputation, neuropathy or other condition. A sensor array includes an array of capacitive force-sensing elements operative to sense axial and shear forces applied to that element. Temperature may also be sensed at each force-sensor location. An electrode matrix, adapted for external placement in an area on a user of the sensor array, includes an array of electrodes in physical correspondence to the array of capacitive sensing elements of the sensor array. An electronic controller is configured to receive electrical signals representative of the axial and shear forces applied to the sensor array and drive the electrode matrix with electrical stimulation signals corresponding to the electrical signals received from the sensor array, thereby enabling the user to experience force and/or temperature sensations experienced by the body part through the electrode matrix.

12 Claims, 3 Drawing Sheets

(56) References Cited

U.S. PATENT DOCUMENTS

2015/0148735 A1* 5/2015 Friedrich ............. A61N 1/0448
604/20
2015/0209212 A1* 7/2015 Duguid ................... A61H 3/00
601/87

* cited by examiner

# MULTICAPACITOR SENSOR ARRAY WITH USER ELECTRICAL FEEDBACK

REFERENCE TO RELATED APPLICATION

This application claims priority to U.S. Provisional Patent Application Serial No. 62/212,896, filed Sep. 1, 2015, the entire content of which is incorporated herein by reference.

FIELD OF THE INVENTION

This invention relates generally to biofeedback and, in particular, to providing electrical feedback to a user who cannot receive full sensation from a body part due to amputation, neuropathy or other condition.

BACKGROUND OF THE INVENTION

Bach-y-Rita's most notable work was in the field of neuroplasticity. He is seen as the first to propose the concept of sensory substitution to treat patients with disabilities, often those caused by neurological problems. One of the first applications of sensory substitution he created was a chair which allowed blind people to 'see'. The trials he conducted in 1969 are now regarded to be the first form of experimental evidence for neuroplasticity and the feasibility of sensory substitution. Later in his career, Bach-y-Rita created a device which enabled patients with damaged vestibular nuclei to regain their ability to remain balanced, by using an electrical stimulator placed on the tongue which reacted to a motion sensor affixed to the patient. This application enabled patients to remain balanced without the equipment after several weeks use.

SUMMARY OF THE INVENTION

This invention is directed to a system and associated methods for providing feedback to a user who cannot receive full sensation from a body part due to amputation, neuropathy or other condition. A sensor array, in contact with a user's body part or prosthetic substitute for a user's body part, includes an array of capacitive elements, each element being operative to sense axial and shear forces applied to that element. An electrode matrix, adapted for external placement in an area on a user of the sensor array, includes an array of electrodes in physical correspondence to the array of capacitive sensing elements of the sensor array. An electronic controller is configured to receive electrical signals representative of the axial and shear forces applied to the sensor array and drive the electrode matrix with electrical stimulation signals corresponding to the electrical signals received from the sensor array, thereby enabling the user to experience force sensations experienced by the body part through the electrode matrix.

In accordance with a preferred embodiment the sensor array also includes an array of temperature sensors operative to sense the temperature at different points in the array, and the controller is further operative to drive the electrode matrix with signals corresponding to the temperature sensed by the temperature sensors. The electrode matrix, adapted for placement on a user's skin or sub-lingual, may be the same size as the sensor array or may be a physically scaled-down version of the sensor array.

The signals delivered to the electrode matrix may be AC or DC signals of a magnitude that causes sensation without pain. The controller is preferably operative to stimulate the electrodes of the electrode matrix in sequential succession, varying aspects of the signals in accordance with the type of force or temperature experienced by the sensor array. The electrical signals delivered to the electrode matrix may be user-variable through a smartphone or other separate electronic device. The smartphone or other electronic device may also act as a data logger enabling a health care provider to monitor the force and/or temperature signals generated by the sensor array over time.

In certain embodiments the sensor array and electrode matrix may be co-located, in a common shoe insert, for example. The electrode matrix may also be used to measure skin resistance, with the controller being further operative to vary the magnitude of the electrical signals delivered to the electrode matrix to compensate for changes in skin resistance. The controller may also be used to sense a user's balance as a function of the electrical signals received from the sensor array.

DETAILED DESCRIPTION OF THE INVENTION

This application relates to providing electrical feedback to humans who have either lost a limb or have diabetes and have neuropathy. A sensor array, preferably in the form of a flexible pad, is placed in a shoe as an insert in the case of the amputee who has lost a foot and the diabetic who has neuropathy and can no longer feel their feet. In the case of an upper body loss of limb, the sensors will be placed mainly in the prosthetic hand, but can also be placed in other parts of the prosthetics such as an elbow.

The sensor array comprises capacitive elements described in U.S. Pat. No. 7,343,813, which describes sensing both axial and shear forces in an array of sensors. The entire content of this issued patent is incorporated herein by reference. In addition to sensing forces the sensor will also sense temperature at each sensor node location. This uses unique circuity that can measure capacitance in the low Pico farad range and also measure a thermistor connected to the same two plates in the matrix.

The sensor circuitry is very insensitive to body capacitance even if it is substantially higher than the capacitance of the plates in the matrix. The circuity is also insensitive to 60 Hz electric fields which are common in homes and businesses.

In addition to providing real time electrical feedback to the human, the system may also transmit data to a receiver device such as a smart phone, smart watch, or tablet computer. This data will be displayed as a physical representation of the forces and temperature. The shear forces can be shown as vectors with the direction of the force being the rotation of the vector, the magnitude of the force(s) being the length of the vector. The axial forces can be displayed as circular balls with the diameter changing with the applied force.

Figure 1:
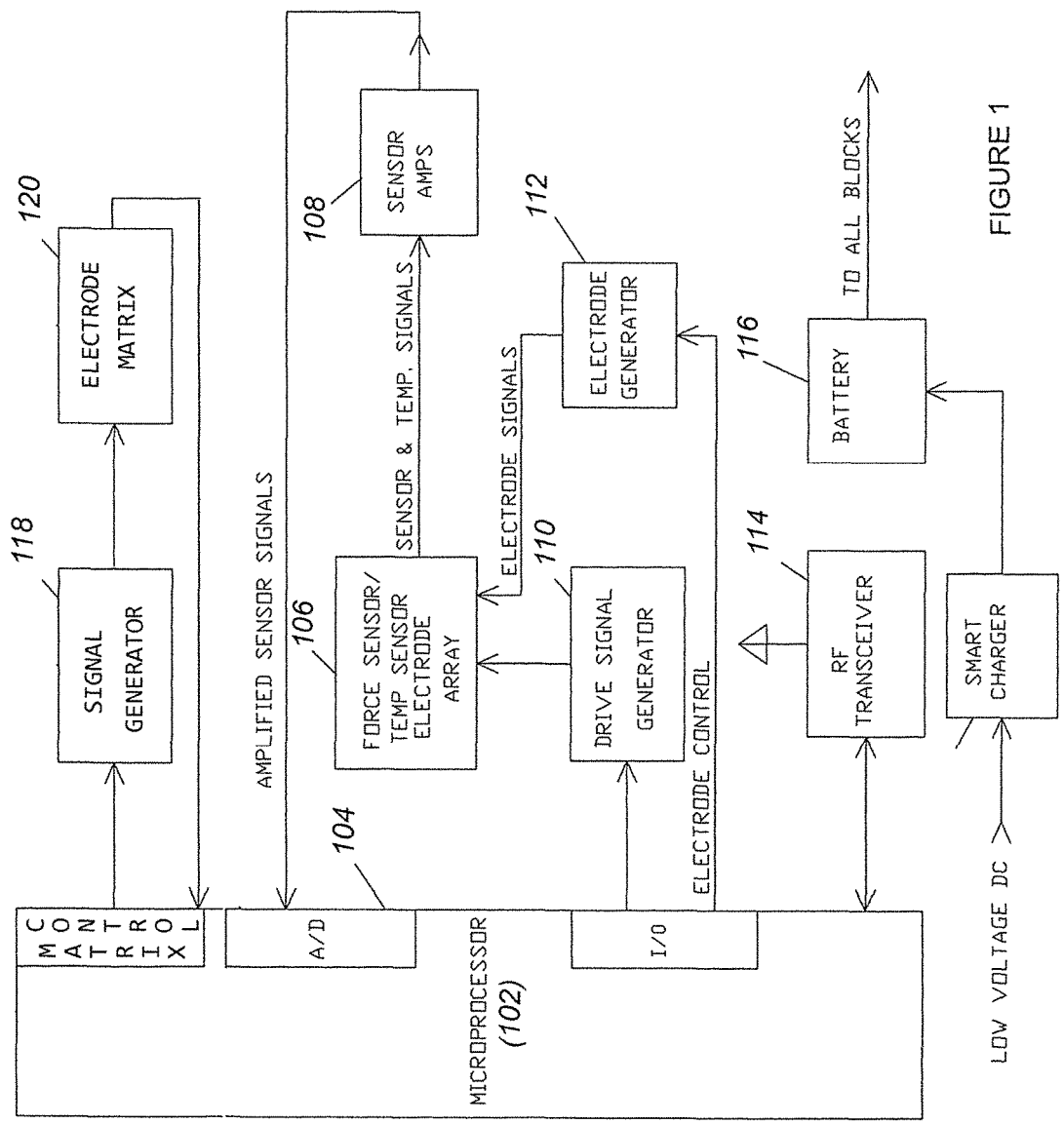
FIG. 1 is block diagram of the system.
Figure 2:
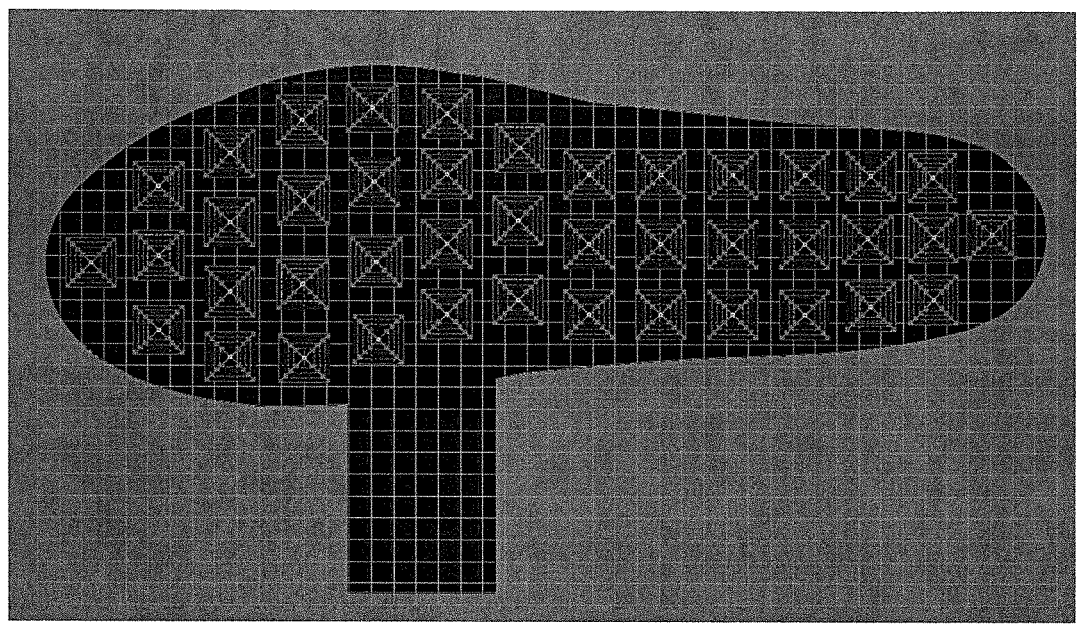
FIG. 2 shows a shoe insert sensor with drive and sense plates.
Figure 3:
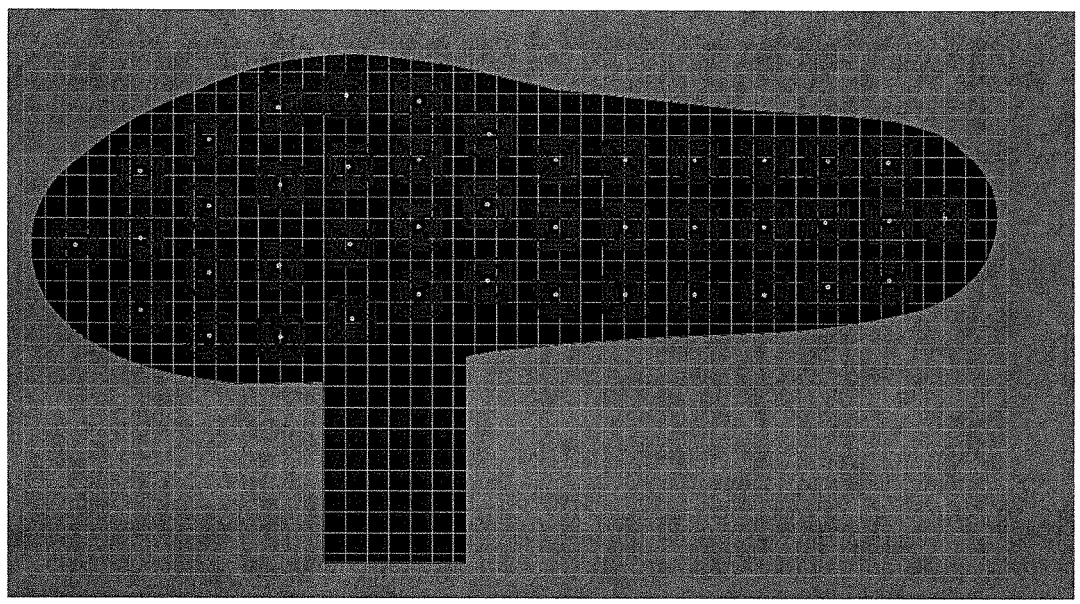
FIG. 3 depicts the shoe insert sense plates.

FIG. 1 is a block diagram of electronic circuitry used to control the system. The real time electrical feedback is generated by an electronic circuit composed of proprietary drive and amplifier circuits that are controlled by an embedded microprocessor 102. These circuits include drive signal generator 110 and electrode generator 112 that activate the force and temperature sensor array 106. The sensor and temperature signals are amplified at 108 and delivered to the micro 102 through analog-to-digital converter 104. The resultant forces and temperature measurements of each cell in the array are then sent to a signal generator 118 that encodes the various forces and temperature into unique voltage and frequency patterns that are connected to an electrode matrix 120. A smart charger is used to convert low-voltage DC to charge battery 116 which supplies power to all circuits in need. RF transceiver 114 is used to remote communications with a smartphone or other electronic device.

The electrode matrix 120 preferably comprises an interdigitated electrode array disposed in a flexible so that the person can move normally and not be hampered by a rigid plate. As such, matrix 120 can be placed anywhere on the body, though there may be optimal places such as the residual limb for the amputee or the calf in the case of the diabetic who's neuropathy is such that they have lost feeling in their feet.

Matrix 120 has a plurality of conductive electrodes arranged in a pattern that resembles the same pattern of sensors in the shoe insert or other form of sensor array. The size of the electrode matrix can be the same size as the shoe insert sensor array, or be scaled up or down to achieve the desired result of transmitting the forces and temperature to the person wearing it. The electrode matrix can be fabricated using flexible printed circuit material with gold plated electrodes. Gold plating is common in the printed circuit manufacturing area with the gold having the attribute of remaining corrosion free. An alternative method of manufacturing the electrode matrix is to use metalized polyurethane. This, too, can be gold plated as the base material is copper and can be electroplated.

The signals on the electrodes of the matrix may be AC or DC. The current and voltage will be carefully controlled by the drive and amplifier circuits. This will limit the current to a few micro-amps using suitable current limiting such as high value resistors. The current will also be monitored by the microprocessor, and it will control the drive and amplifier circuits to supply the correct current and voltage to make it large enough for the persons nerves to monitor it, but not so large that it is dangerous or painful.

The electrodes will preferably be stimulated one at a time; all other electrodes will be at ground potential as a reference and will allow a small current to flow between the stimulated electrode and all the other electrodes. Ideally, the level will be so low that the person will not even feel it, but will have sensations in their feet that were missing before the sensor and electrode system was installed. For the amputee, the phantom limb issue can be a problem, and this invention can make it feel real again and help the amputee walk and feel better.

The electrode signals will be different for each parameter measured. The axial forces (normal forces) may have a distinct waveform such as a sine wave or a square wave, or a triangle wave with the amplitude being proportional to the force being measured. The frequency of the axial force signals can be different from the frequency of the shear sensors. The temperature sensing signals will be different than either of the force sensors; for example, a high amplitude pulse at a fixed rate.

Electrode voltages and waveforms can be changed by the user via the smart phone or other device in radio contact with the sensing array. In this way, comfort and learning can be achieved. The smart phone or other smart device can serve as a data logger and can also send the data files to the doctor or prosthetist who in treating them so that adjustments to the system can done to improve their health.

The electrode matrix may be interleaved with the sensor matrix for the early stage diabetic experiencing the initial stages of neuropathy. First, the physical relationship between the forces and temperature would be identical, and second, the electrical stimulus may create a reversal of neuropathy by creating new cell growth. It is well known that electromagnetic fields stimulate bone growth, as this technique is commonly used for stress fractures of bones. A matrix of electrodes will also generate an electromagnetic field and could help new cell generation.

To teach the user's brain about the different forces and temperature, preferably only one of the parameters such as axial forces (normal force) will be sent at a predetermined time period. Next only the shear forces for some unit of time are sent until the brain's neurons form a distinct pattern and associate it with the shear forces, axial forces or temperature. Temperature signals are sent separately, the same as the force signals, until the brain learns about foot temperature. Temperature may be sent the same way independent of its actual value, hot or cold, both are problematic. After the brain has had time to learn the different signal patterns, the system can be altered to send multiple patterns to the electrodes such as axial and shear forces and temperature at the same time.

Decreased blood circulation may cause a foot ulcer to form, this decreased circulation may cause skin temperature to initially decrease until infection arises and then the temperature will increase. Measuring all the temperatures in the array and noting a difference at one place in the foot is a prime indicator that a problem may be occurring. Noting a difference in temperature at one place in the foot is very different than most or all of the temperatures rising or falling as this may be due to environmental changes, however if several sensor nodes that are adjacent to each other are rising, then it may be the onset or infection, or shoe that is not the right size for the individual (too big, and the foot is rubbing and the friction is causing heat). Sending this temperature data to the smart phone, watch or other device allows the diabetic or amputee to prevent a serious ulcer from forming. The same is true for amputees at the residual limb socket interface, in this case the sensor array may be placed in the socket where the residual limb is. Amputees also are plagued with pressure ulcers which may really be caused be shear forces. Measuring both the shear and axial forces along with temperature in the socket will be a great benefit to the amputee.

Given that the skin resistance varies from person to person and also with perspiration which make the skin much more conductive, a method of making this more predictable is desirable. One acceptable method is to apply conductive solution or gel to electrodes for a more predictable skin resistance. This conductive solution is used for ECG electrodes and is readily available.

The electrode matrix could also be used to measure the skin resistance and vary the electrode voltage to compensate for changes. This measurement could also be used to prompt the person to remove the matrix pad and clean the electrodes, skin reapply the conductive grease and reapply the matrix pad.

The placement of the electrode matrix can be on the leg, residual limb, back or tongue or other place on the body that makes sense for the particular situation. The leg, back or residual limb is preferred over the tongue, though some encouraging results have been achieved with using it (i.e., Bach-y-Rita's).

Yet another application of the invention is for people with balance problems. The combination of the multi-capacitor sensor array along with the electrical stimulation will help people keep their balance. The measurement of multiple axial sensors in both feet will indicate that an imbalance is occurring. For instance if the all the axial sensors on the outside on the person's foot are measuring substantially more force than the middle or right side, and the forces on the other foot are decreasing a substantial amount, the person is starting to fall sideways. The electrical stimulation of the outside on the person's foot that is measuring substantially more force than the middle will be applied so that the brain will activate the nerves that activate the muscle to prevent the fall. In conjunction with the multi-capacitor sensor array along with the electrical stimulation, MEMS tilt sensors along with rate gyros could also be of great benefit. The more sensor inputs to the microprocessor, the better it could determine if the person is starting to fall, or simply starting to walk or turn or sit down.

The use of vibratory actuators in the place of electrical stimulation is also possible and will achieve some of the same benefits such as the brain learning how the person is walking, and how to keep them from falling. This may be Piezo electric devices such as Macro Fiber Composite (MFC) made by Smart Materials. These devices will be operated the same as the electrical stimulation such that they oscillate in the same physical relationship as the sensors. The frequency of the oscillations will correlate with the forces, axial force being one frequency, and shear forces being another frequency. Temperature will be sent as a unique code that is distinguishable from the forces.

The invention claimed is:

1. A system for providing feedback to a user who cannot receive full sensation from a body part due to amputation, neuropathy or other condition, the system comprising:
    a sensor array in contact with a user's body part or prosthetic substitute for a user's body part, the sensor array including an array of capacitive elements arranged in a two-dimensional pattern, each element being operative to sense axial and shear forces applied to that element;
    an electrode matrix adapted for external placement on an area of a user's skin, the electrode matrix having an array of electrodes arranged in a two-dimensional pattern that corresponds to the two-dimensional pattern of the capacitive sensing elements of the sensor array;
    wherein the correspondence between the sensor array and the electrode matrix is a one-to-one correspondence such that for every capacitive element in the sensor array pattern there is a corresponding electrode in the electrode matrix pattern; and
    an electronic controller configured to receive electrical signals representative of the axial and shear forces applied to the sensor array and drive the electrode matrix with electrical stimulation signals corresponding to the electrical signals received from the sensor array, thereby enabling the user to experience force sensations experienced by the body part through the electrode matrix.

2. The system of claim 1, wherein:
    the sensor array also includes an array of temperature sensors operative to sense the temperature at different points in the array; and
    the controller is further operative to drive the electrode matrix with signals corresponding to the temperature sensed by the temperature sensors.

3. The system of claim 1, wherein the electrode matrix is the same size as the sensor array or wherein the electrode matrix is a physically scaled-down version of the sensor array.

4. The system of claim 1, wherein the signals delivered to the electrode matrix are AC or DC signals of magnitude that causes sensation without pain.

5. The system of claim 1, wherein the controller is operative to stimulate the electrodes of the electrode matrix in sequential succession.

6. The system of claim 1, wherein the electrical signals delivered to the electrode matrix vary in accordance with the type of force experienced by the sensor array.

7. The system of claim 1, wherein the electrical signals delivered to the electrode matrix are user variable through a smartphone or other separate electronic device.

8. The system of claim 1, wherein:
    the electrical signals delivered to the electrode matrix are user variable through a smartphone or other electronic device; and
    the smartphone or other electronic device further functions as a data logger enabling a health care provider to monitor the electrical signals generated by the sensor array over time.

9. The system of claim 1, wherein the sensor array and electrode matrix are co-resident in a common insert.

10. The system of claim 1, wherein:
    the electrode matrix is also used to measure skin resistance; and
    the controller is operative to vary the magnitude of the electrical signals delivered to the electrode matrix to compensate for changes in skin resistance.

11. The system of claim 1, wherein the controller is further operative to sense a user's balance as a function of the electrical signals received from the sensor array.

12. The system of claim 1, wherein the electrode matrix includes vibratory actuators.

* * * * *